United States Patent [19]

Reinicke

[11] Patent Number: 4,684,365

[45] Date of Patent: Aug. 4, 1987

[54] DISPOSABLE REFILL UNIT FOR IMPLANTED MEDICATION INFUSION DEVICE

[75] Inventor: Robert H. Reinicke, Mission Viejo, Calif.

[73] Assignee: Eaton Corporation, Cleveland, Ohio

[21] Appl. No.: 786,213

[22] Filed: Oct. 10, 1985

Related U.S. Application Data

[63] Continuation-in-part of Ser. No. 694,707, Jan. 24, 1985, abandoned.

[51] Int. Cl.[4] .......................... A61M 5/16; A61J 1/00
[52] U.S. Cl. .................................... 604/126; 604/413
[58] Field of Search ................ 604/126, 45, 118, 122, 604/129, 190, 233–235, 240–243, 268, 272, 405, 406, 411–415, 891, 896

[56] References Cited

U.S. PATENT DOCUMENTS

| | | | |
|---|---|---|---|
| Re. 29,656 | 6/1978 | Chittenden et al. | 604/413 |
| 2,778,360 | 1/1957 | Miskel | 604/190 |
| 2,864,366 | 12/1958 | Miskel | 604/243 |
| 2,973,758 | 3/1961 | Murrish | 604/413 |
| 3,480,014 | 11/1969 | Callahan | 604/415 |
| 3,967,621 | 7/1976 | Schwarz | 604/241 |
| 4,173,222 | 11/1979 | Muetterties | 604/246 |
| 4,190,048 | 2/1980 | Sampson | 604/175 |
| 4,398,544 | 8/1983 | Nugent et al. | 604/240 |
| 4,505,709 | 3/1985 | Froning et al. | 604/411 |

Primary Examiner—Stephen C. Pellegrino
Attorney, Agent, or Firm—D. A. Rowe; L. G. Vande Zande

[57] ABSTRACT

A refill unit for a negative pressure type implanted infusion device includes a hollow cylindrical housing member which is adapted to receive at one end a bottle of vacuum conditioned medication. As the bottle is inserted first and second needles or tubes penetrate the closure member of the bottle, the shorter one of these needles being positioned to receive medication inside the bottle and the longer one extends into the ullage space of the bottle when it is inserted and held vertically. The shorter needle communicates with a refill needle, which extends downwardly from the other end of the cylindrical member, through a membrane type filter which is hydrophilic to the medication and has a micron rating such that the filter once it is wetted can pass air bubbles but only at a differential pressure substantially greater than the negative pressure differential of the implanted device. The longer needle communicates with ambient air through a membrane type filter which is hydrophobic to the medication and permits the unobstructed flow of air into the ullage space of the bottle while preventing air-borne bacteria from entering this air space.

33 Claims, 9 Drawing Figures

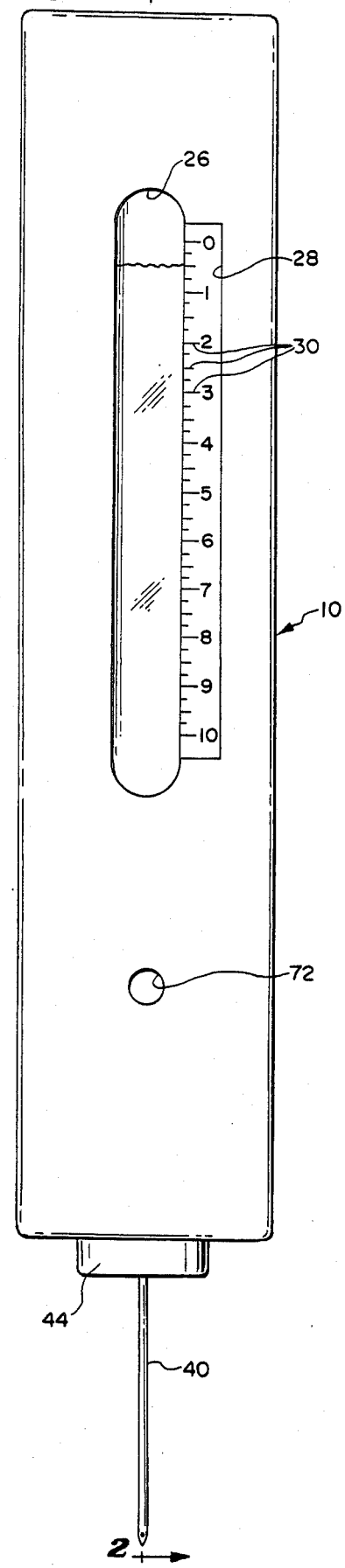
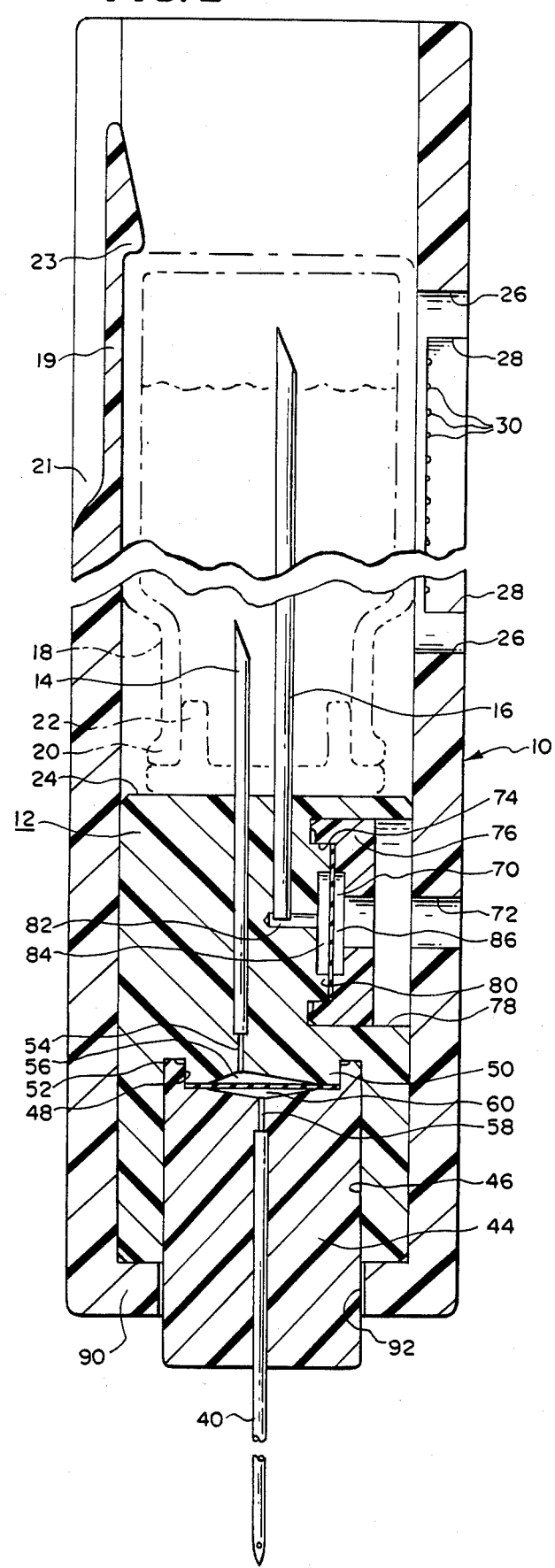
FIG. 1
FIG. 2

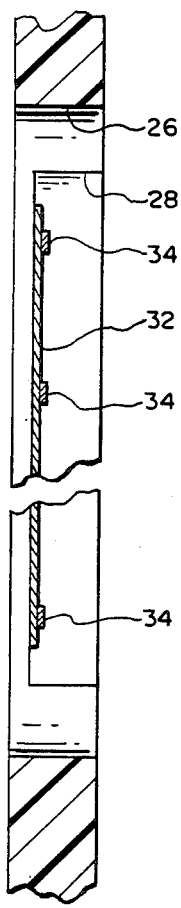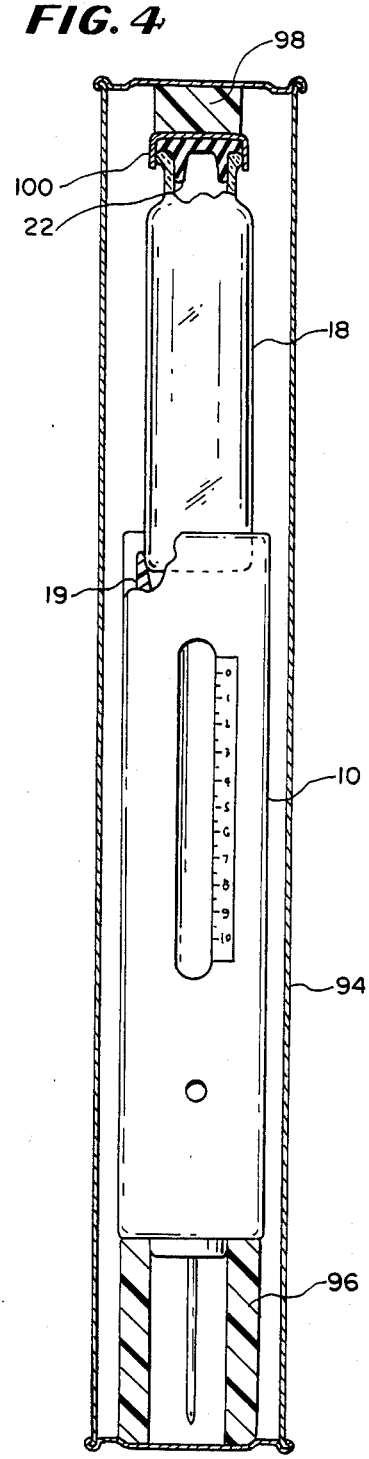

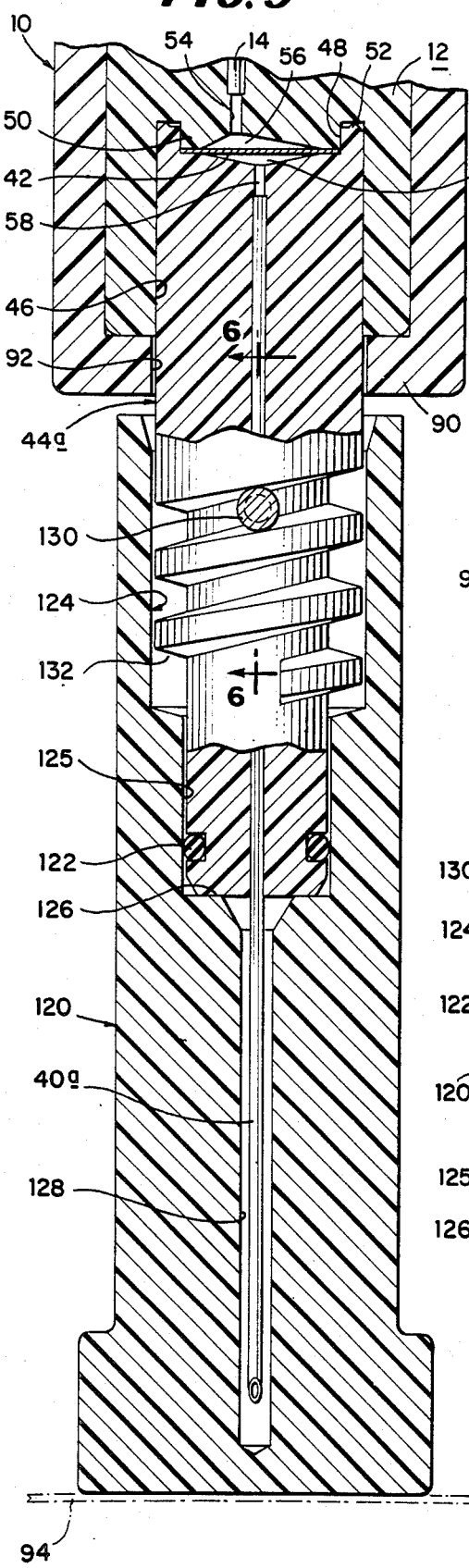
FIG. 5
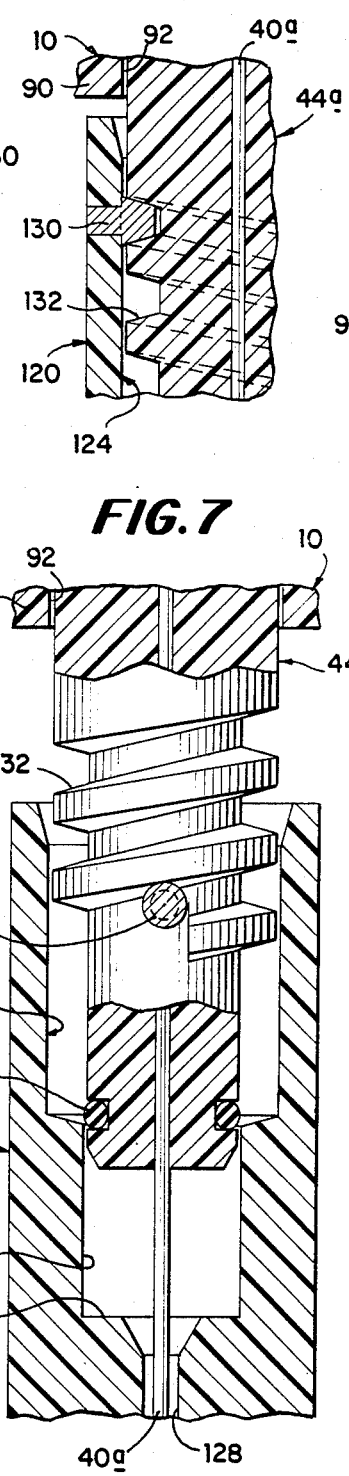
FIG. 6
FIG. 7
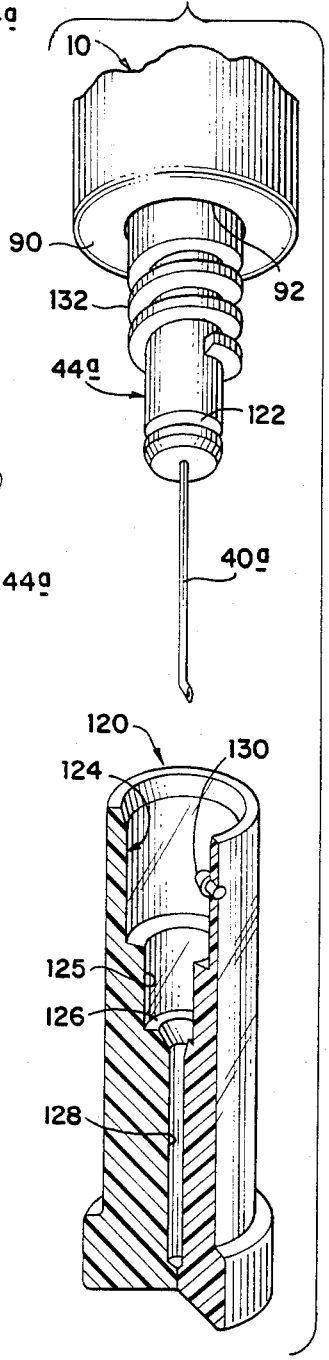
FIG. 8
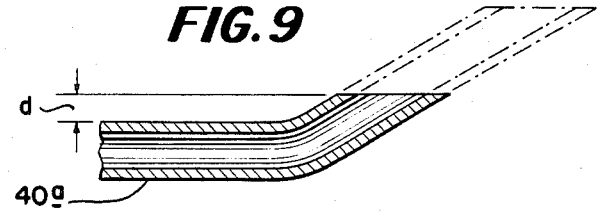
FIG. 9

DISPOSABLE REFILL UNIT FOR IMPLANTED MEDICATION INFUSION DEVICE

The present application is a continuation-in-part of Reinicke application Ser. No. 694,707, filed Jan. 24, 1985, now abandoned.

BACKGROUND OF THE INVENTION

The present invention relates to arrangements for refilling the medication reservoir of an implanted medication infusion device, and, more particularly, to a disposable unit for refilling an infusion device of the type having means for maintaining the medication reservoir at a pressure substantially less than the pressure of the body in which the device is implanted.

Various types of implantable medication infusion devices have been heretofore proposed as shown, for example, in Haerten et al U.S. Pat. No. 4,077,405, Franetzki et al. U.S. Pat. No. 4,191,181, Portner et al. U.S. Pat. No. 4,265,241, Ellinwood U.S. Pat. No. 3,692,027, Tucker et al. U.S. Pat. No. 3,951,147, and Blackshear et al U.S. Pat. No. 3,731,681. In general, the refilling of the medication reservoir of such devices after they have been implanted in the body is accomplished by a conventional hypodermic needle and syringe, as shown in Haerten et al U.S. Pat. No. 4,077,405. Also, the arrangement shown in Sampson U.S. Pat. No. 4,190,048 may be employed to refill such devices.

In Franetzki U.S. Pat. No. 4,191,181, and in my copending application Ser. No. 554,197 filed Nov. 22, 1983, the implanted device is provided with means for maintaining the medication reservoir at a pressure substantially less than the pressure in the body in which the device is implanted. Such a negative pressure device can be refilled using a conventional hypodermic needle and piston syringe by simply letting the natural pressure differential from the ambient to the negative pressure reservoir pull the medication out of the syringe and into the implanted device. With such an arrangement the natural pressure differential may not be sufficient at high altitude to overcome the friction in the seals of the piston syringe. Also, the danger is always present that the piston could be inadvertently pushed and produce a pressure above body pressure which could accidently infuse a potentially lethal dose of medication into the patient's body if the needle of the external refill device does not initially engage the septum of the implanted device properly or becomes disengaged (due to motion of the patient or other reasons) before the refill is finished. Furthermore, the conventional hypodermic needle and piston syringe is not airtight and if used in a negative pressure type of implanted device presents a problem due to the fact that the tiniest bit of air leaking through the piston syringe will be immediately sucked into the reservoir. This is particularly undesirable in negative pressure type implanted devices which employ a pulsatle pump to infuse medication into the body, such as described in my above-identified copending application Ser. No. 554,197 which are quite sensitive to the presence of air in the medication reservoir. Extreme care must be exercised during the refilling operation to be sure that air bubbles are not introduced into the reservoir along with the desired medication. The requirement that the medication introduced into the reservoir be free of air bubbles is in addition to the further requirements that the conditions under which the medication is introduced are intrinisically safe with respect to avoiding accidental gross infusion of medication into the patient and maintaining sterility of the medication during the refill process.

SUMMARY OF THE INVENTION

The arrangement of the present invention is particularly adapted to solve the problems encountered in refilling negative pressure type implanted medication infusion devices and to obviate the above discussed difficulties encountered in connection therewith. Furthermore, the refill unit of the present invention is inexpensive to manufacture and can be used as a disposable unit in connection with a refilling operation from a small (such as 10 or 25 milliliter) bottle of vacuum conditioned (degassed) medication in a simple and reliable manner without introducing air bubbles into the reservoir of the negative pressure implanted device.

Briefly considered, the refill unit includes a hollow cylindrical housing member which is adapted to receive at one end a bottle of vacuum conditioned medication. As the bottle is inserted first and second needles or tubes penetrate the closure member of the bottle, the shorter one of these needles being positioned to receive medication inside the bottle and the longer one extends into the ullage space of the bottle when it is inserted and held vertically. Accordingly, the present invention avoids the need for transferring medication from the original medicine bottle to a separate refill unit container thus avoiding attendant sterility and contamination control concerns.

The shorter needle communciates with a refill needle, which extends downwardly from the other end of the cylindrical member, through a membrane type filter which is hydrophilic to the medication and has a micron rating such that the filter once it is wetted can pass air bubbles but only at a differential pressure substantially greater than the negative pressure differential of the implanted device. The longer needle communicates with ambient air through a membrane type filter which is hydrophobic to the medication and permits the unobstructed flow of air into the ullage space of the bottle while preventing airborne bacteria from entering this air space.

In accordance with an important aspect of the present invention the refill unit is sterile packaged, together with the bottle of medication to be used, in a metal can which is evacuated to provide a vacuum packed unit. If the bottle of medication happens to be vacuum conditioned by the manufacturer the vacuum jacketing in this metal can provides extra assurance that the medication will remain vacuum conditioned. If the medication is not vacuum conditioned by the manufacturer, as is usually the case, the medication will become vacuum conditioned due to permeation through the bottle closure member (septum) during a deliberate pre-storage period before the medication is used. For example, it has been found that a minimum storage of 100 hours is sufficient to vacuum condition medication in a 10 milliliter bottle having a silicone septum. Obviously, this pre-storage period will vary with the thickness and material of the septum used, as well as its sealing characteristic.

The refill unit of the present invention is particularly adapted to function with such a vacuum conditioned bottle of medication and provide bubble-free introduction of the medication into the implanted device because the total volume of the passageways, filter cavities and needles of the refill unit is very small, i.e. less than 10 microliters (1/100 of a milliliter) so that the refill unit can be used without being purged of air before the refill operation which greatly simplifies the refill apparatus and procedure. This small amount of air is easily absorbed by the vacuum conditioned medication which is introduced into the reservoir of the implanted device during the refill operation. Even a small bottle (10 milliliters) of vacuum conditioned medication will hold 100 microliters of air before it becomes air saturated and introduces air bubbles which can reduce the efficiency (bolus size or infusion rate) or even completely disable the operation of the implanted device. Accordingly, the refill unit of the present invention provides a completely safe and simple means for refilling negative pressure implanted devices with vacuum conditioned bubble-free medication.

BRIEF DESCRIPTION OF THE DRAWINGS

The invention, both as to its organization and method of organization, together with further objects and advantages there-of, will best be understood by reference to the following specification taken in connection with the accompanying drawings, in which:

FIG. 1 is a side elevational view of the refill unit of the present invention;

FIG. 2 is a sectional view taken along the lines 2—2 of FIG. 1 showing the refill unit on a somewhat larger scale;

FIG. 3 is a fragmentary sectional view of an alternative embodiment of the refill unit of the present invention;

FIG. 4 is a side elevational view of the refill unit of FIG. 1 showing the manner in which this unit is preferably vacuum packaged together with a bottle of medication in accordance with the present invention;

FIG. 5 is a fragmentary side elevational view of an alternative embodiment of the invention;

FIG. 6 is a sectional view, taken along line 6—6 of FIG. 5;

FIG. 7 is a view similar to FIG. 5 but showing the needle guard in partially withdrawn position;

FIG. 8. is an exploded perspective view of the embodiment of FIG. 5; and

FIG. 9 is a sectional side elevational view of the preferred needle tip arrangement of the present invention.

Referring now to the drawings, and more particularly to FIGS. 1-4, the refill unit of the present invention is therein illustrated as comprising a hollow cylindrical housing indicated generally at 10 in one end of which there is positioned a manifold member indicated generally at 12. A first relatively short tube or needle 14 and a second relatively long tube or needle 16 are mounted aside each other in the manifold member 12, the upper ends of the tubes 14 and 16 being sharpened so that when an inverted bottle 18 of medication is inserted into the open upper end of the housing 10 the tubes 14 and 16 will puncture the septum portion 20 of the closure member or stopper 22 of the bottle 18 as this bottle is moved into engagement with the upper surface 24 of the manifold 12. The bottle 18 is held in the position shown in FIG. 2 during the refilling operation by a spring arm 19 which is formed in the slot 21 provided in the side wall of the housing 10, the arm 19 having the hook portion 23 which engages the bottom of the bottle 18 and holds it in place.

The housing 10 is preferably provided with an elongated opening 26 in the sidewall thereof through which the bottle 18 can be viewed. This sidewall portion is also provided with an elongated recess 28 along one side of the opening 26, a suitable indicator scale 30 being molded in the bottom surface of the recess 28 at the time the housing 10 is formed. In the alternative, a separate indicator scale 32 (FIG. 3) may be slideably mounted in the recess 28 by means of the molded arms 34 which hold the scale 32 against the bottom surface of the recess 28. In the embodiment of FIGS. 1 and 2 the scale 30 is employed to measure the amount of medication which has been supplied to the implanted medication infusion device by noting the level of the liquid in the bottle 18 at the beginning and end of the refill operation. In the embodiment of FIG. 3 the scale 32 can be adjusted so that the zero point is in line with the level of the liquid at the start of the refill operation, thereby simplifying the measurement of the amount of liquid introduced during the refill operation. In this connection, it will be noted that in FIG. 1 the medicine bottle 18 is longer and smaller in diameter than most standard medicine bottles. Although this is not necessary, such a bottle shape provides for more accurate visual resolution of the medication level in the bottle and the reading error due to the bottle not being positioned perfectly vertical is thereby reduced.

The tube 14 communicates with a downwardly extending needle 40 through a membrane type filter 42, the needle 40 extending out of the bottom end of the housing member 10 and being adapted to be inserted through the skin into the penetrable septum of the implanted medication infusion device. For example, the needle 40 may be percutaneously inserted into the septum 62 of the implanted medication infusion device shown in my copending application Ser. No. 554,197 filed Nov. 22, 1983. The needle 40 is preferably 1 to 2 inches long so the septum of the implanted device will be fully penetrated, even if the device should move inwardly and further away from the skin surface. Although a side-ported pencil point tip ("Whitacre" style) needle 40 of about 23 gauge size is shown in FIG. 2 that will not core the elastomer septum material and be occluded or blocked, alternate non-coring needle point styles can be used, such as a side-ported (sometimes called a deflected point or "Huber") needle. The Whitacre point is less likely to kick up a burr due to pressure against the needle stop in the implanted device, and thus will not damage the septum upon removal, although the patient will feel more discomfort upon initial penetration because its point is "duller".

The needle 40 is mounted in a retainer member 44 which is arranged to be positioned in a bottom opening 46 formed in the manifold member 12. The membrane type circular filter disk 42 is first inserted into the annular recess 48 formed in the upper end of the retainer 44 after which the retainer 44 is inserted into the recess 46 in the manifold 12 until the filter disk 42 is seated on a depending annular seat portion 50 formed in the recess 46 of the manifold 12. The retainer 44 is then secured to the manifold 12 with the filter disk 42 tightly held on the annular seat 50 by the retainer 44. If desired, the retainer 44 may be secured within the recess 46 by ultrasonic (or Radio Frequency) welding in which case the retainer 44 is provided with a lip portion 52 on the upper edge thereof which is melted during the ultrasonic welding operation, pressure being applied to the retainer 44 to hold the filter disk 42 on the annular seat 50 during this welding operation. In the alternative, the lip 52 may be eliminated and the retainer 44 secured within the recess 46 by a suitable adhesive, or by solvent bonding of the members 44 and 12.

The tube 14 communicates with the upper side of the filter disk 42 through the passageway 54 and the cavity 56 formed in the manifold 12, the walls of the cavity 56 being sloped as indicated in FIG. 2 to minimize the volume of the cavity 56. The needle 40 communicates with the underside of the filter 42 through the passage 58 and the recess 60 formed in the retainer 44, the walls of the recess 60 being sloped to minimize the volume of this cavity, as shown in FIG. 2, and to prevent the entrapment of bubbles in this cavity so that the exit side of the membrane filter disk 42 is always wetted.

In accordance with an important aspect of the present invention, the filter disk 42 is a membrane type filter having a micron rating such that the "bubble point" of the filter, i.e. the pressure differential which must be exceeded for air to go through the filter disk 42 when wetted, is substantially greater than the pressure differential of the implanted negative pressure medication infusion device. Preferably, the membrane filter 42 has a micron rating of approximately 0.22 microns. Such a filter characteristically has a bubble point of approximately 50 psid. Since the bottom or exit side of the filter disk 42 always remains wetted, this filter disk can easily block passage of air bubbles at the 7 psid pressure differential (15 psia ambient minus a typical 8 psia in the reservoir of the implanted negative pressure device) that would exist across the filter disk 42 in the event that the bottle 18 runs dry before the reservoir of the implanted device is filled. In such an event, the reservoir can be topped-off by using a second medicine bottle and refill unit to complete the filling process. Accordingly, the passage of air bubbles during the refill operation is positively prevented by providing a membrane filter disk 42 which has a rating of 0.22 microns. The filter disk 42 may comprise a Durapore filter manufactured by the Millipore Corp. and is preferably hydrophilic to the medication within the bottle 18 so that it readily absorbs the medication and allows it to pass freely during the refill process but does not permit the passage of air bubbles therethrough since it remains wetted on the exit side during the entire refill operation.

The tube 16 which extends to the ullage space 36 of the bottle 18, communicates with ambient air through a filter disk 70 and an opening 72 in the sidewall of the cylindrical housing 10. More particularly, the filter disk 70 is positioned in an annular recess 74 formed in a retainer member 76 which is inserted into the side opening recess 78 formed in the manifold 12. The filter disk 70 is seated on an annular seat portion 80 formed in the bottom of the recess 78 in the manifold 12 and the retainer 76 is secured in place with the filter disk 70 securely seated on the annular seat 80 by any suitable means such as by an adhesive, solvent bonding, or by ultrasonic welding, as discussed in detail previously in connection with the retainer 44. The tube 16 communicates with the left hand side of the filter disk 70 through the passage 82 and the recess 84 formed in the manifold 12. The right hand side of the filter disk 70 communicates with the ambient air through the recess 86 formed in the retainer 76 and the opening 72 in the sidewall of the housing 10.

The filter disk 70 is preferably a membrane type filter which prevents air borne bacteria from entering the air space 36 within the bottle 18. Preferably, the filter disk 70 is hydrophobic to the medication within the bottle 18 so that it will not absorb this medication and thus permits the unobstructed flow of air into the ullage space of the bottle during the refill process. The filter disk 70 may likewise be a Durapore type filter manufactured by the Millipore Corp. and has a rating of approximately 0.22 microns to block most airborne bacteria. Both of the filter disks 42 and 70 are made of polyvinylidene difluoride but the disk 42 is processed to be hydrophilic to medication and the disk 70 is processed to be hydrophobic to medication.

In assembly, the filter disk 42 is first placed in the annular recess 48 of the retainer 44 and this retainer 44 is then positioned in the manifold 12 with the filter disk 42 securely seated on the annular seat portion 50 thereof after which the retainer 44 is secured to the manifold 12. In a similar manner, the filter disk 70 is first inserted into the annular recess 74 of the retainer 76 and this retainer is then mounted in the opening 78 of the manifold 12, the retainer 76 being secured to the manifold 12 while the filter disk 70 is securely seated on the annular seat 80 of the manifold recess 78. After these filter disks have been inserted, the manifold assembly is then inserted into the housing 10 until it rests upon the end wall 90 thereof with the retainer 44 extending downwardly through the opening 92 formed in this end wall, the manifold 12 then being secured in this position within the housing 10 by any suitable means such as adhesives or by ultrasonic welding.

The housing 10, the manifold 12 and the retainers 44 and 76 are all preferably made of injection molded medical grade plastic, such as a polycarbonate, so that the entire refill unit may be readily manufactured at low cost to provide a disposable refill unit. Also, as discussed generally heretofore, the refill unit is preferably sterile packaged together with the bottle of medication to be used in a metal can. More particularly, as shown in FIG. 4 a narrow, cylindrical metal container 94 is provided in which the refill unit and bottle 18 are packaged with the bottom end of the bottle 18 positioned within the open upper end of the housing 10. To protect the needle 40 a tubular spacer member 96 is positioned between the bottom of the housing 10 and the bottom of the can 94. Also, a protective spacer 98 may be positioned between the top of the bottle 18, and the top of the can 94. The bottle 18 conventionally has a metal cap 100 over the stopper 22 thereof which is removed prior to inserting the inverted bottle into the housing 10. After the refill unit, bottle 18 and members 96 and 98 are positioned in the can 94, the can is evacuated to provide a vacuum packed refill unit. The can 94 preferably has a readily removable top, similar to a tennis ball can, and the doctor or nurse who opens the can has an audible signal as the can is opened that the bottle 18 is vacuum conditioned.

In the alternative, the refill unit 10 can be sterile packaged externally to and separate from the vacuum jacketed medication bottle 18. However, placing the refill unit 10 within the same can as the medicine bottle provides assurance that the refill device will "fit" the medicine bottle and avoid mix ups due to handling.

If the bottle of medication 18 happens to be vacuum conditioned by the manufacturer the vacuum jacketing provided by the metal can 94 provides extra assurance that the medication will remain vacuum conditioned. If the medication is not vacuum conditioned by the manufacturer, as is usually the case, the medication will become vacuum conditioned due to permeation through the bottle closure member 22 (the septum portion which is pierced by the tubes 14 and 16) during a deliberate prestorage period before the medication is used. For example, it has been found that a minimum storage of 100 hours is sufficient to vacuum condition medication in a 10 milliliter bottle 18 having a silicone septum. Obviously, this prestorage period will vary with thickness and type of septum used, as well as the sealing characteristic between the septum and bottle.

It will also be noted that the refill unit of the present invention is particularly adapted to function with such a vacuum conditioned bottle of medication and provide bubble free introduction of the medication into the implanted device because the total volume of the passageways 54 and 58, the filter cavities 56 and 60, the tube 14 and the needle 40 is very small, i.e., is less than 10 microliters. As a result, the refill unit can be used without being purged of air before the refill operation which greatly simplifies the refill procedure. A small amount of air, such as 5 to 10 microliters, is easily absorbed by the vacuum conditioned medication which is provided in the bottle 18 and introduced into the reservoir of the implanted device during the refill operation. Even a small bottle (10 milliliters) of vacuum conditioned medication will hold 100 microliters air before it becomes air saturated and can reduce the efficiency (bolus size or infusion rate) or even completely disable the operation of the implanted device. Accordingly the refill unit of the present invention provides a completely safe and simple means for refilling negative pressure implanted devices with vacuum conditioned bubble-free medication.

In the embodiment of the invention shown in FIGS. 1-4, inclusive, described above, the total volume of the needles 14, 40, the passageways 54 and 58 and the cavities 56 and 60 on either side of the filter 42 is purposely made quite small so that the small amount of air contained therein can readily be absorbed by the vacuum conditioned medication in the bottle 18 and it is not necessary to purge the refill unit of air before using it. However, when this total volume is very small a prolonged period of time is required to refill the implanted infusion device due to the restrictive nature of the passageways involved. On the other hand, if these passageways are made relatively large to permit the rapid flow of medication into the implanted device, then some means must be provided to purge the air from these passageways before the needle 40 is inserted into the implanted device. In the embodiment of FIGS. 5-9, inclusive, an arrangement is provided for automatically purging the refill unit of air as it is prepared for use so that large passageways can be used and the implanted device may be refilled very quickly. In this embodiment, elements which are similar to the embodiment of FIGS. 1-4 have been given the same reference characters. Referring to FIGS. 5 to 9, in this embodiment the needle guard 96 of the embodiment of FIGS. 1-4 is replaced by a needle guard 120 which is sealed to the member 44a by means of the O ring 122. The needle guard 120 is provided with a recess 124 in the end thereof and a recess 125 of smaller diameter which are adapted to receive the member 44a. The bottom end of the member 44a is seated on the bottom wall 126 of the recess 125 when the refill unit is stored in the metal can 94, as described in detail heretofore. The recess 125 communicates with a smaller central recess 128 which is adapted to receive the needle 40a which extends out of the bottom of the member 44a.

When the needle guard 120 is removed from the end of the member 44 a vacuum is created in the recesses 125 and 128, due to the sealing action of the O ring 122, which sucks medication out of the bottle 18, through the tube 14, the passageways 54, 58 and the cavities 56, 60 and through the needle 40a so that the entire refill system is purged of air automatically as the needle guard 120 is removed to prepare the refill unit for use. As a result, all of these passageways and cavities may be quite large so that medication can flow freely from the bottle 18 and the implanted medication infusion device can be refilled quickly. Preferably, these passageways and cavities are sufficiently large that a 10 milliliter infusion device can be refilled in less than two minutes. The needle guard 120 is preferably made of a clear plastic material so that the operator can determine by visual inspection that medication is flowing out of the tip of the needle 40a and that the refill system has been purged of air.

If the needle guard 120 is pulled off of the member 44a very fast it is possible that the medication will vaporize when the pressure in the passageway 128 gets down to about 1 psia. In order to prevent such a situation, the member 44a may, if desired, have the thread 132 formed in the portion thereof which is positioned within the recess 124. The thread 132 is of relatively coarse pitch and cooperates with an inwardly extending pin 130 in the wall of the needle guard 120 so that one or two revolutions of the needle guard 120 are required to remove the needle guard 120 from the end of the member 44a. However, the pin 130 and thread 132 positively prevent the needle guard 120 from being pulled off of the member 44a at high speed with the possible attendant vaporization of the medication in the refill system. As shown in FIG. 5, the thread 132 is spaced from the O ring 122 mounted on the bottom end of the member 44a so that the needle guard 120 remains sealed to the member 44a as it is rotated. Due to the coarse pitch of the thread 132 the space between the O ring 122 and the bottom wall 126 of the recess 124 rapidly increases as the needle guard is rotated so that the refill system is purged of air by the time the pin 130 has moved to the end of the thread 112 to permit complete removal of the needle guard 120. It will be noted that by providing the thread 132 on the outer surface of the member 44a and the pin 130 which is mounted in the wall of the needle guard after it is formed, all parts of the disposable refill unit of FIGS. 5-9 may be molded of suitable plastic material at low cost. As an alternate to the pin 130, a thread can be provided in the inner wall of the needle guard.

While the needle 40a may have a side-ported pencil point tip ("Whitacre" style), as discussed above in connection with FIG. 2, such a needle is quite expensive to manufacture due to the fact that the pencil tip has to be welded and ground to a pencil point after which the side port has to be drilled. Accordingly, such an expensive needle is not particularly desirable for use in the disposable refill unit of the present invention. In accordance with a further aspect of the invention a deflected tip, or Huber type of needle, is modified so that the offset of the deflected tip portion is minimized. More particularly, as shown in FIGS. 8 and 9, particularly FIG. 9, the conventional deflected tip or Huber point, shown in dotted lines in FIG. 9 is cut off so that the maximum offset "d" (FIG. 9) of the deflected tip is preferably less than 0.010 inches when a 23 gauge needle is used. It has been found that such a modified Huber point for the needle 40a minimizes the trauma on the septum of the implanted infusion device during the piercing process and permits an implanted device to be refilled many more times without damaging the septum. In this connection, it should be pointed out that the septum of an implanted infusion device is usually much thicker than the septum provided in medication bottles, such as the bottle 18, and hence the conventional Huber point shown in dotted lines in FIG. 9 is considerably harder on the septum due to the change in angle of the elongated deflected tip portion. However, by modifying the deflected tip so that it preferably has a maximum offset "d" of less than 0.010 inches it has been found that the septum will last for at least 500 punctures, and often more than 1000 or 1500 punctures. Also, the modified Huber point of the present invention is more patient comfortable than the conventional Huber point shown in dotted lines in FIG. 9.

Obviously, many modifications and variations of the present invention are possible in light of the above teachings. Thus it is to be understood that, within the scope of the appended claims, the invention may be practiced otherwise than as specifically described hereinabove.

I claim:

1. A medication refill arrangement for an implanted medication infusion device of the type having a medication reservoir and means for maintaining said reservoir at a pressure substantially less than the pressure of the body in which the device is implanted, comprising a hollow tubular member, a manifold member secured in one end of said tubular member carrying first and second tubes extending into the interior of said tubular member, said first and second tubes being adapted to be inserted through the closure member of a medication bottle which is placed in the other end of said tubular member and moved into engagement with said tubes with sufficient force to cause said tubes to penetrate said closure member, said first tube communicating with the medication in said bottle after penetration of said closure member, said first tube communicating with the medication in said bottle after penetration of said closure member and said second tube communicating with the ullage space within said bottle, a hollow needle positioned in said manifold member opposite said tubes and extending outwardly from said one end of said tubular member, means defining a first passageway in said manifold extending between said first tube and said hollow needle, an opening in a sidewall of said tubular member, and means defining a second passageway in said manifold extending between said second tube and said sidewall opening.

2. The refill arrangement of claim 1, which includes first and second filter means positioned respectively in said first and second passageways.

3. The refill arrangement of claim 2, wherein said first and second filter means comprise membrane type medication filters.

4. The refill arrangement of claim 3, wherein said first and second membrane filters each have a rating of approximately 0.22 microns.

5. The refill arrangement of claim 2, wherein said second filter means is effective to prevent air-borne bacteria from entering the ullage space of said bottle through said second passageway and said second tube.

6. The refill arrangement of claim 5, wherein said second filter means is hydrophobic to the medication in said bottle, thereby to permit the unobstructed flow of air through said second filter means and into the ullage space of said bottle.

7. The refill arrangement of claim 2, wherein said first filter means is hydrophilic to the medication in said bottle and permits the free flow of medication to said hollow needle while preventing air bubbles from entering said needle even if the bottle is emptied of medication during the refilling operation.

8. The refill arrangement of claim 2, wherein said first filter means is a membrane type filter having a micron rating such that air bubbles will not pass therethrough at the differential pressure which exists between said reservoir and said bottle during the refilling operation.

9. The refill arrangement of claim 8, wherein said first filter means has a rating of approximately 0.22 microns.

10. The refill arrangement of claim 1, wherein said manifold has a bottom opening recess therein, means defining an annular seat in said recess, a filter disk positioned on said annular seat, and a retainer member positioned within said recess to hold said filter disk against said annular seat, said first passageway including a first portion extending from said first tube to the upper side of said filter disk and a second portion in said retainer and extending from the lower side of said filter disk to said needle.

11. The refill arrangment of claim 10, wherein said retainer is provided with an annular portion outside said filter disk to facilitate the positioning of said filter disk on said annular seat.

12. The refill arrangement of claim 1, wherein said manifold has a side opening recess therein, means defining an annular seat in said recess, a filter disk positioned on said annular seat, and a retainer positioned within said recess to hold said filter disk against said annular seat, said second passageway including a first portion extending from said second tube to one side of said filter disk and a second portion in said retainer extending from the other side of said disk to said sidewall opening.

13. The refill arrangement of claim 12, wherein said retainer is provided with an annular portion outside said filter disk to facilitate the positioning of said filter disk on said annular seat.

14. A medication refill arrangement for an implanted medication infusion device of the type having a medication reservoir and means for maintaining said reservoir at a pressure substantially less than the pressure of the body in which the device is implanted, comprising a tubular member carrying a tube positioned in one end thereof extending into the interior of the tubular member which is adapted to be inserted through the closure member of a medication bottle which is positioned within said tubular member and moved into engagement with said tube with sufficient force to cause said tube to penetrate the closure member, a hollow needle extending outwardly from said one end of said tubular member and adapted to be inserted into the implanted medication infusion device for percutaneously refilling the reservoir thereof, means defining a passageway between said tube and said needle; and a sleeve positioned on said one end of said tubular member and enclosing said needle, said sleeve being removable from said one end of said tubular member while maintaining a sealed connection thereto so that removal of said sleeve is effective to pull medication through said tube, said passageway and said needle and remove air therefrom.

15. The arrangement of claim 14, wherein said one end of said tubular member includes a cylindrical projection through which said needle extends, said sleeve enclosing said needle and at least a portion of said cylindrical projection, and an O ring positioned between said projection and said sleeve to maintain a sealed relationship therebetween as said sleeve is removed from said projection.

16. The arrangement of claim 15 which includes thread means interconnecting said projection and said sleeve so that said sleeve must be rotated to be removed from said projection, thereby to prevent too rapid a removal of said sleeve from said projection.

17. The arrangement of claim 15, wherein said sleeve is made of a transparent material so that the flow of medication out of the end of said needle as said sleeve is removed from said projection can be visually checked.

18. The arrangement of claim 16, wherein said thread means are positioned so that said O ring maintains said sealed relationship between said sleeve and said projection as said sleeve is rotated.

19. The arrangement of claim 16, wherein said thread means is spaced a substantial distance away from said O ring along the length of said cylindrical projection so that said sleeve can be rotated several revolutions while said O ring maintains said sealed relationship between said sleeve and said projection.

20. A medication refill arrangement for an implanted medication infusion device of the type having a medication reservoir and means for maintaining said reservoir at a pressure substantially less than the pressure of the body in which the device is implanted, comprising a tubular member carrying a tube positioned in one end thereof extending into the interior of the tubular member which is adapted to be inserted through the closure member of a medication bottle which is positioned within said tubular member and moved into engagement with said tube with sufficient force to cause said tube to penetrate the closure member, a hollow needle extending outwardly from said one end of said tubular member and adapted to be inserted into the implanted medication infustion device for percutaneously refilling the reservoir thereof, means defining a passageway between said tube and said needle; a needle guard positioned on said one end of said tubular member and having a cavity therein within which said needle is positioned, and means for sealing said cavity while permitting said needle guard to be moved in the direction to increase the volume of said cavity, whereby upon movement of said needle guard in said direction medication is sucked out of the bottle through said tube, said passageway and said needle to remove air therefrom.

21. The arrangement of claim 20, which includes a membrane type medication filter positioned in said passageway, said filter having a micron rating such that air bubbles will not pass therethrough at the differential pressure which exists between said reservoir and said bottle during the refilling operation.

22. The arrangement of claim 21, wherein said membrane type filter has a rating of approximately 0.22 microns.

23. The arrangement of claim 20, which includes a hydrofilic membrane type filter positioned in said passageway which allows medication to pass freely through said passageway to said needle during the refilling process while preventing air bubbles from entering said implanted device.

24. A medication refill arrangement for an implanted medication infusion device of the type having a medication reservoir and means for maintaining said reservoir at a pressure substantially less than the pressure of the body in which the device is implanted, comprising a housing having a recess for receiving a bottle of medication, a tube mounted in said housing and adapted to penetrate the closure member of the medication bottle when it is inserted into said recess, a hollow needle extending from said housing and adapted to be inserted into the implanted medication infusion device for percutaneously refilling the reservoir thereof, means defining a passageway between said tube and said needle, a needle guard having a cavity which is adapted to receive said needle, and means for maintaining said cavity sealed from the atmosphere while permitting movement of said needle guard in the direction to increase the volume of said cavity, whereby upon movement of said needle guard in said direction medication is sucked out of the bottle and through said tube said passageway and said needle to remove air therefrom.

25. The arrangement of claim 24 including means for allowing said needle guard to be completely removed from said needle after the air has been removed from said needle by movement of said needle guard in said direction.

26. The arrangement of claim 24, including means for allowing said needle to be visible as said needle guard is moved in said direction so that the flow of medication out of said needle after air is remvoed therefrom can be verified.

27. The arrangement of claim 24, which includes a cylindrical member connected to said housing and having said needle secured therein and extending therefrom along the axis thereof, said needle guard including a sleeve portion adapted to fit over said cylindrical member, and means for sealing said sleeve to said cylindrical member while permitting said needle guard to be moved along said axis to increase the volume of said cavity.

28. The arrangement of claim 27, wherein said sealing means comprises an O ring mounted on said cylindrical member and in engagement with the inside surface of said sleeve.

29. The arrangement of claim 28, which includes thread means interconnecting said cylindrical member and said sleeve so that said needle guard must be rotated to be removed from said needle.

30. The arrangement of claim 29, wherein said thread means has a coarse pitch so that only a few revolutions of said needle guard produce a substantial movement of said needle guard in said direction.

31. The arrangement of claim 14, which includes a membrane type medication filter position in said passageway, said filter having a micron rating such that air bubbles will not pass therethrough at the differential pressure which exists between said reservoir and said bottle during the refilling operation.

32. The arrangement of claim 31, wherein said membrane type filter has a rating of approximatley 0.22 microns.

33. The arrangement of claim 14 which includes a hydrofilic membrane type filter positioned in said passageway which allows medication to pass freely through said passageway to said needle during the refilling process while preventing air bubbles from entering said implanted device.

* * * * *